(12) United States Patent
Nath et al.

(10) Patent No.: US 9,322,013 B2
(45) Date of Patent: Apr. 26, 2016

(54) MAGNETIC SEPARATION OF ALGAE

(71) Applicant: Los Alamos National Security, LLC, Los Alamos, NM (US)

(72) Inventors: Pulak Nath, Los Alamos, NM (US); Scott N. Twary, Santa Fe, NM (US)

(73) Assignee: Los Alamos National Security, LLC, Los Alamos, NM (US)

( * ) Notice: Subject to any disclaimer, the term of this patent is extended or adjusted under 35 U.S.C. 154(b) by 0 days.

(21) Appl. No.: 14/189,969

(22) Filed: Feb. 25, 2014

(65) Prior Publication Data

US 2014/0242663 A1    Aug. 28, 2014

Related U.S. Application Data

(60) Provisional application No. 61/768,991, filed on Feb. 25, 2013.

(51) Int. Cl.
 *C12N 13/00* (2006.01)
 *C12N 1/02* (2006.01)
 *C12N 1/12* (2006.01)

(52) U.S. Cl.
 CPC *C12N 13/00* (2013.01); *C12N 1/02* (2013.01); *C12N 1/12* (2013.01)

(58) Field of Classification Search
 None
 See application file for complete search history.

(56) References Cited

U.S. PATENT DOCUMENTS

| | | | | |
|---|---|---|---|---|
| 6,099,738 | A * | 8/2000 | Wechsler et al. | 210/695 |
| 6,432,630 | B1 * | 8/2002 | Blankenstein | 435/4 |
| 2009/0162919 | A1 * | 6/2009 | Radaelli et al. | 435/257.6 |
| 2012/0196339 | A1 | 8/2012 | Koppisch et al. | |
| 2013/0210064 | A1 | 8/2013 | Nath et al. | |

FOREIGN PATENT DOCUMENTS

GB    2335656 A *    9/1999

OTHER PUBLICATIONS

Godel, S et al. Flagellar membrane proteins of Tetraselmis striata Butcher (Chlorophyta). Protist. 2000. 151: 147-159.*
Allen et al, "FeA1, FeA2, and FrE1, Encoding Two Homologous Secreted Proteins and a Candidate Ferrireductase, Are Expressed Coordinately with FOX1 and FTR1 in Iron-Deficient *Chlamydomonas reinhardtii*," *Eukaryotic Cell*, vol. 6, pp. 1841-1852, 2007.
Arakaki et al., "A Novel Protein Tightly Bound to Bacterial Magnetic Particles in *Magnetospirillum magneticum* Strain AMB-1," *The Journal of Biological Chemistry*, vol. 278, pp. 8745-8750, 2003.
Chothia et al., "The relation between the divergence of sequence and structure in proteins," *The EMBO Journal*, vol. 5, No. 4, pp. 823-826, 1986.
De Araujo et al., "Magnetite and Magnetotaxis in Algae," *Biophys. J.*, vol. 50, pp. 375-378, 1986.
Dillow, "Genetically Modified Algae Are Magnetic, for Ease of Manipulation," *Popular Science*, 2011, available on the World Wide Web popsci.com/science/article/2011-10/scientists-create-magnetic-algae-can-be-manipulated-magnet (1 page).
Greenspan et al., "Defining epitopes: It's not as easy as it seems," *Nature Biotechnology*, vol. 17, pp. 936-937, 1999.
Mikayama et al., "Molecular cloning and functional expression of a cDNA encoding glycosylation-inhibiting factor," *Proc. Natl. Acad. Sci. USA*, vol. 90, pp. 10056-10060, 1993.
Nakamura et al., "An Iron-regulated Gene, magA, Encoding an Iron Transport Protein of *Magnetospirillum* sp. Strain AMB-1," *The Journal of Biological Chemistry*, vol. 270, pp. 28392-28396, 1995.
Prozorov et al, "Protein-Mediated Synthesis of Uniform Superparamagnetic Magnetite Nanocrystals," *Adv. Funct. Mater.*, vol. 17, pp. 951-957, 2007.
Rudinger et al., "Characteristics of the amino acids as components of a peptide hormone sequence," *Peptide Hormones*, pp. 1-7, 1976.
Tanaka et al., "MMS6 Protein Regulates Crystal Morphology during Nano-sized Magnetite Biomineralization in Vivo," *The Journal of Biological Chemistry*, vol. 286, pp. 6386-6392, 2011.
Timko et al., "Magnetic Properties and Heating Effect in Bacterial Magnetic Nanoparticles," *Journal of Magnetism and Magnetic Materials*, vol. 321, pp. 1521-1524, 2009.
Xie et al., "Production, Modification and Bio-Applications of Magnetic Nanoparticles Gestated by Magnetotactic Bacteria," *Nano. Res.*, vol. 2, pp. 261-278, 2009.
Zurkiya et al, "MagA is Sufficient for Producing Magnetic Nanoparticles in Mammalian Cells, Making It an MRI Reporter," *Magnetic Resonance in Medicine*, vol. 59, pp. 1225-1231, 2008 (Abstract Only).
Bitton et al., "Removal of algae from Florida lakes by magnetic filtration," *Appl. Microbiol.*, vol. 30, pp. 905-908, 1975.
Cerff et al., "Harvesting fresh water and marine algae by magnetic separation: Screening of separation parameters and high gradient magnetic filtration," *Bioresource Technology*, vol. 118, pp. 289-295, 2012.
Grima et al., "Recovery of Microalgal Biomass and Metabolites: Process Options and Economics," *Biotechnology Advances*, vol. 20, pp. 491-515, 2003.
Liu et al., "Removal of algal blooms from freshwater by the coagulation—magnetic separation method," *Environ. Sci. Pollut. Res*, vol. 20, pp. 60-65, 2013.
Lim et al., "Rapid Magnetophoretic Separation of Microalgae," *Small* vol. 8, pp. 1683-1692, 2012.
Xu et al., "A simple and rapid harvesting method for microalgae by in situ magnetic separation," *Bioresource Technology* vol. 102, pp. 10047-10051, 2011.

* cited by examiner

*Primary Examiner* — Renee Claytor
*Assistant Examiner* — Susan E Fernandez
(74) *Attorney, Agent, or Firm* — Klarquist Sparkman, LLP

(57) ABSTRACT

Described herein are methods and systems for harvesting, collecting, separating and/or dewatering algae using iron based salts combined with a magnetic field gradient to separate algae from an aqueous solution.

6 Claims, 2 Drawing Sheets

MAGNETIC SEPARATION OF ALGAE

CROSS REFERENCE TO RELATED APPLICATIONS

This claims the benefit of U.S. Provisional Application No. 61/768,991, filed Feb. 25, 2013, which is incorporated herein by reference in its entirety.

ACKNOWLEDGMENT OF GOVERNMENT SUPPORT

This invention was made with government support under Contract No. DE-AC52-06NA25396 awarded by the U.S. Department of Energy. The government has certain rights in the invention.

FIELD

The present disclosure relates generally to methods and systems for harvesting, collecting, separating and/or dewatering algae using magnetic based separation techniques.

BACKGROUND

One of the challenges faced by biofuel production from microalgae is that, traditionally, the organisms must be harvested and dewatered to reduce the overall processing volume and improve the efficiency of the extraction process. Standard methods available are filtration, centrifugation, sedimentation (or settling), flocculation and membrane filtration. While most of these methods are adapted from existing industrial applications, they suffer from such disadvantages as being time consuming, having significant energy requirements, producing unwanted heat, and being expensive.

Ultrasonic filtration is being investigated for algae harvesting. This approach uses acoustic radiation force to concentrate algae. However, operation of acoustic transducers requires electrical energy input, and the transducers generate significant heat, which needs to be regulated (using additional energy) to avoid unwanted algae lysis.

Commercial centrifuges are the most common instruments being used in algae-based biofuel industries. However, like ultrasonic filtration, operating centrifuges requires electrical energy to operate, and the energy requirement scales proportionally with the volume of operation. Further, this method is labor intensive. In addition, because of the large amount of water involved, centrifugation is cost prohibitive.

Settling, in either holding tanks or plate type settling devices, is an inexpensive though time-consuming process. This method is ill-suited for dewatering algae because of the small size and low specific gravity of algal cells. The length of the settling process for algae poses several difficulties, especially in a production plant where the cells being collected will either be used in a downstream process or for extraction of oil. First, the long processing time decreases plant throughput. Second, it increases the likelihood of contamination that can compromise downstream processing. The long-term storage of the cells associated with settling can lead to decay or reabsorption of the product of interest (e.g., oil, pigments, secondary metabolites, and other co-products) for cell maintenance that can compromise product extraction efficiency and yields.

Chemical flocculation is another harvesting technique, in which specific chemicals are used to flocculate (create aggregates of) the algae. However, this method relies on sedimentation, which is time consuming.

Membrane filtration is also being investigated; however, membrane filters require significant maintenance to avoid clogging.

In recent years, there has been interest in using magnetic means for algae harvesting. However, current approaches require the creation of transgenic algae and/or magnetic beads or nanoparticles, which are time consuming and costly to develop and maintain.

Therefore, there continues to be a need for alternative composition and methods for improved, cost-effective and efficient biomass and biofuel production systems, particularly large-scale systems.

SUMMARY

The present disclosure describes a method comprising exposing an aqueous solution comprising algae and an iron supplement to a magnetic field gradient of at least about 50 Tesla/meter, whereby the method results in the algae being separated from the aqueous solution. Embodiments of the disclosed methods remove or minimize disadvantages of previous harvesting methods, and reduce costs associated with standard harvesting methods.

In one embodiment, the iron supplement is in the form of an iron salt. In one example, the iron salt in the aqueous solution is at a concentration of about at least 300 µM. In other examples, the iron salt in the aqueous solution is at a concentration of from about 300 µM to about 1000 µM (or about 300 µM, 350 µM, 400 µM, 450 µM, 500 µM, 550 µM, 600 µM, 650 µM, 700 µM, 750 µM, 800 µM, 850 µM, 900 µM, 950 µM or 1000 µM). In particular examples, the iron salt is biocompatible with algae. In some examples, the iron salt is selected from the group consisting of $FeSO_4$; $FeBr_2$; $FeBr_3$; $FeCl_2$; $FeCl_3$; $FeF_2$; $FeF_3$; $FeI_2$; $FeMoO_4$; $(NH_4)_2Fe(SO_4)_2 \cdot 6H_2O$; $C_{20}H_{20}Cl_2FeN_4$; $FeCl_2 \cdot 4H_2O$; $C_6H_5FeO_7$; $FeF_3 \cdot 3H_2O$; $Fe(NO_3)_3 \cdot 9H_2O$; $Fe(C_2O_4) \cdot 2H_2O$; $Fe_2(C_2O_4)_3 \cdot 6H_2O$; $Fe(ClO_4)_2 \cdot xH_2O$; $Fe(ClO_4)_3 \cdot H_2O$; $FePO_4 \cdot 4H_2O$; $Fe_4(P_2O_7)_3$; $FeSO_4 \cdot xH_2O$; $Fe_2(SO_4)_3 \cdot xH_2O$; $Fe(BF_4)_2 \cdot 6H_2O$; $K_4Fe(CN)_6 \cdot 3H_2O$ and a combination of two or more thereof.

In yet another example, the magnetic field gradient is at least about 100 Tesla/meter, such as at least about 500 Tesla/meter. In one example, the magnetic field gradient is at least about 1000 Tesla/meter. In another example, the magnetic field gradient is from about 500 Tesla/meter to about 1000 Tesla/meter (or 500 Tesla/meter; 550 Tesla/meter; 600 Tesla/meter; 650 Tesla/meter; 700 Tesla/meter; 750 Tesla/meter; 800 Tesla/meter; 850 Tesla/meter; 900 Tesla/meter; 950 Tesla/meter or 1000 Tesla/meter). In some examples, the magnetic field gradient is generated by a permanent magnet.

In some embodiments, the algae are wild-type algae (such as non-transgenic algae) or transgenic algae. Optionally, the algae are *Tetraselmis striata*.

The present disclosure further describes a method comprising exposing an aqueous solution comprising algae and an iron salt at a concentration of at least about 100 µM to a magnetic field gradient having sufficient strength to separate the algae from the aqueous solution whereby the method results in the algae being separated from the aqueous solution.

In one example, the iron salt in the aqueous solution is at a concentration of at least about 300 µM. In some examples, the iron salt in the aqueous solution is at a concentration of from about 100 µM to about 1000 µM (or about 100 µM, 150 µM, 200 µM, 250 µM, 300 µM, 350 µM, 400 µM, 450 µM, 500 µM, 550 µM, 600 µM, 650 µM, 700 µM, 750 µM, 800 µM, 850 µM, 900 µM, 950 µM or 1000 µM). In related aspect, the iron salt is biocompatible with algae. In a related aspect, the iron salt is selected from the group consisting of $FeSO_4$; $FeBr_2$; $FeBr_3$;

$FeCl_2$; $FeCl_3$; $FeF_2$; $FeF_3$; $FeI_2$; $FeMoO_4$; $(NH_4)_2Fe(SO_4)_2 \cdot 6H_2O$; $C_{20}H_{20}Cl_2FeN_4$; $FeCl_2 \cdot 4H_2O$; $C_6H_5FeO_7$; $FeF_3 \cdot 3H_2O$; $Fe(NO_3)_3 \cdot 9H_2O$; $Fe(C_2O_4) \cdot 2H_2O$; $Fe_2(C_2O_4)_3 \cdot 6H_2O$; $Fe(ClO_4)_2 \cdot xH_2O$; $Fe(ClO_4)_3 \cdot H_2O$; $FePO_4 \cdot 4H_2O$; $Fe_4(P_2O_7)_3$; $FeSO_4 \cdot xH_2O$; $Fe_2(SO_4)_3 \cdot xH_2O$; $Fe(BF_4)_2 \cdot 6H_2O$; $K_4Fe(CN)_6 \cdot 3H_2O$ and a combination of two or more thereof.

In some examples, the magnetic field gradient is at least about 50 Tesla/meter, such as about 200 Tesla/meter or about 400 Tesla/meter. In another example, the magnetic field gradient is at least about 600 Tesla/meter. In aspect still further example, the magnetic field gradient is at least about 1000 Tesla/meter. In some examples, the magnetic field gradient is from about 400 Tesla/meter to about 1000 Tesla/meter (or 500 Tesla/meter; 550 Tesla/meter; 600 Tesla/meter; 650 Tesla/meter; 700 Tesla/meter; 750 Tesla/meter; 800 Tesla/meter; 850 Tesla/meter; 900 Tesla/meter; 950 Tesla/meter or 1000 Tesla/meter). In particular examples, the magnetic field gradient is generated by a permanent magnet.

In some examples, the algae are wild-type algae (such as non-transgenic algae) or transgenic algae. Optionally, the algae are *Tetraselmis striata*.

The present disclosure further describes a system for separating algae from an aqueous solution, the system comprising a source having an aqueous solution containing algae and at least a first conduit having a first volume carrying capacity that carries the aqueous solution containing algae from the source, wherein the first conduit further includes an iron supplement (for example, including at least one iron salt at a concentration of at least about 100 µM) and is in close proximity to a magnet having a magnetic field gradient having sufficient strength to separate the algae from the aqueous solution (for example, at least about 500 Tesla/meter), and wherein the algae are collected in the first conduit. In some examples, the aqueous solution containing the algae in the source optionally includes an iron supplement.

In other embodiments, the system includes at least a first conduit having a first volume carrying capacity that carries the aqueous solution containing algae (and optionally an iron supplement) from the source to a second conduit having a second volume carrying capacity, wherein the second conduit is in close proximity to a magnet having a magnetic field gradient having sufficient strength to separate the algae from the aqueous solution (for example, at least about 500 Tesla/meter), wherein the aqueous solution in the second conduit includes an iron supplement (for example, including at least one iron salt at a concentration of at least about 100 µM) and wherein the algae are collected in the second conduit. In some examples, the second volume carrying capacity of the second conduit is larger than the first volume carrying capacity of the first conduit. In other examples, the second volume carrying capacity of the second conduit is about the same as the first volume carrying capacity of the first conduit. In a further example, the second conduit is adjacent to the magnet.

In some examples, the iron supplement is in the form of an iron salt. In some examples, the iron salt in the aqueous solution is at a concentration of at least about 100 µM. In further examples, the iron salt in the aqueous solution is at a concentration of from about 300 µM to about 1000 µM (or about 300 µM, 350 µM, 400 µM, 450 µM, 500 µM, 550 µM, 600 µM, 650 µM, 700 µM, 750 µM, 800 µM, 850 µM, 900 µM, 950 µM or 1000 µM). In related aspect, the iron salt is biocompatible with algae. In particular examples, the iron salt is selected from the group consisting of $FeSO_4$; $FeBr_2$; $FeBr_3$; $FeCl_2$; $FeCl_3$; $FeF_2$; $FeF_3$; $FeI_2$; $FeMoO_4$; $(NH_4)_2Fe(SO_4)_2 \cdot 6H_2O$; $C_{20}H_{20}Cl_2FeN_4$; $FeCl_2 \cdot 4H_2O$; $C_6H_5FeO_7$; $FeF_3 \cdot 3H_2O$; $Fe(NO_3)_3 \cdot 9H_2O$; $Fe(C_2O_4) \cdot 2H_2O$; $Fe_2(C_2O_4)_3 \cdot 6H_2O$; $Fe(ClO_4)_2 \cdot xH_2O$; $Fe(ClO_4)_3 \cdot H_2O$; $FePO_4 \cdot 4H_2O$; $FeO_2O_7)_3$; $FeSO_4 \cdot xH_2O$; $Fe_2(SO_4)_3 \cdot xH_2O$; $Fe(BF_4)_2 \cdot 6H_2O$; $K_4Fe(CN)_6 \cdot 3H_2O$ and a combination of two or more thereof.

In some examples, the magnetic field gradient is at least about 600 Tesla/meter. In another example, the magnetic field gradient is at least about 1000 Tesla/meter. In a further example, the magnetic field gradient is from about 400 Tesla/meter to about 1000 Tesla/meter (or 500 Tesla/meter; 550 Tesla/meter; 600 Tesla/meter; 650 Tesla/meter; 700 Tesla/meter; 750 Tesla/meter; 800 Tesla/meter; 850 Tesla/meter; 900 Tesla/meter; 950 Tesla/meter or 1000 Tesla/meter). In some examples, the magnetic field gradient is generated by a permanent magnet. In some examples, the magnetic field gradient is from a permanent magnet, electromagnet or a combination thereof. In other examples, the magnetic field gradient is from a Halbach array.

In particular examples, the algae are wild-type algae (such as non-transgenic algae) or transgenic algae. Optionally, the algae are *Tetraselmis striata*.

The foregoing and other objects, features, and advantages of the invention will become more apparent from the following detailed description, which proceeds with reference to the accompanying figures.

DETAILED DESCRIPTION

I. Terms and Methods

Figure 1:
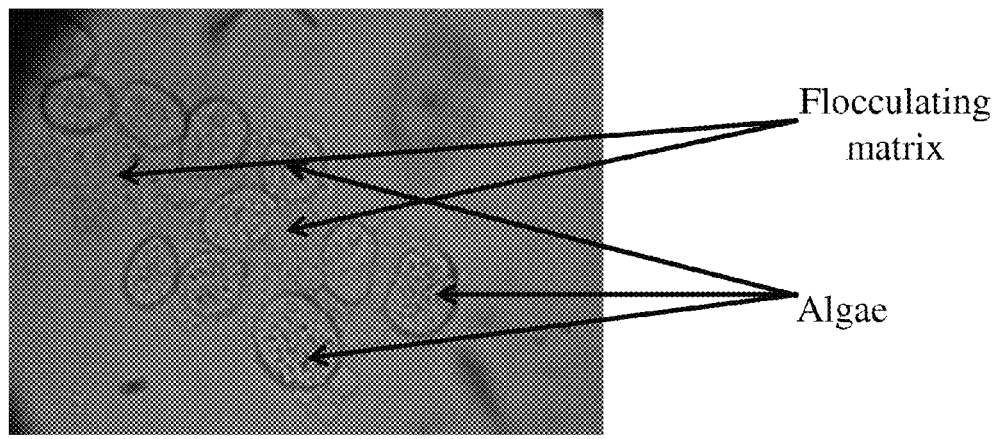
FIG. 1 shows a light microscope observation of an algae floc after the addition of ferric salts to the culture. The flocculating matrix surrounding the algae is visible.

Unless otherwise noted, technical terms are used according to conventional usage. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

In order to facilitate review of the various embodiments of the disclosure, the following explanations of specific terms are provided:

Algae: Algae, as used herein, refers to algae species that can be used with the compositions and methods described herein and include for example, *Achnanthes orientalis*, *Agmenellum* spp., *Amphiprora hyaline*, *Amphora coffeiformis*, *Amphora coffeiformis* var. *linea*, *Amphora coffeiformis* var. *punctata*, *Amphora coffeiformis* var. *taylori*, *Amphora*

*coffeiformis* var. *tenuis, Amphora delicatissima. Amphora delicatissima* var. *capitata, Amphora* sp., *Anabaena, Ankistrodesmus, Ankistrodesmus falcatus, Boekelovia hooglandii, Borodinella* sp., *Botryococcus braunii, Botryococcus sudeticus, Bracteococcus minor, Bracteococcus medionucleatus, Carteria, Chaetoceros gracilis, Chaetoceros muelleri, Chaetoceros muelleri* var. *subsalsum, Chaetoceros* sp., *Chlamydomonas perigranulata, Chlorella anitrata, Chlorella antarctica, Chlorella aureoviridis, Chlorella Candida, Chlorella capsulate, Chlorella desiccate, Chlorella ellipsoidea, Chlorella emersonii, Chlorella fusca, Chlorella fusca* var. *vacuolata, Chlorella glucotropha, Chlorella infusionum, Chlorella infusionum* var. *actophila, Chlorella infusionum* var. *auxenophila, Chlorella kessleri, Chlorella lobophora, Chlorella luteoviridis, Chlorella luteoviridis* var. *aureoviridis, Chlorella luteoviridis* var. *lutescens, Chlorella miniata, Chlorella minutissima, Chlorella mutabilis, Chlorella nocturna, Chlorella ovalis, Chlorella parva, Chlorella photophila, Chlorella pringsheimii, Chlorella protothecoides, Chlorella protothecoides* var. *acidicola, Chlorella regularis, Chlorella regularis* var. *minima, Chlorella regularis* var. *umbricata, Chlorella reisiglii, Chlorella saccharophila, Chlorella saccharophila* var. *ellipsoidea, Chlorella salina, Chlorella simplex, Chlorella sorokiniana, Chlorella* sp., *Chlorella sphaerica, Chlorella stigmatophora, Chlorella vanniellii, Chlorella vulgaris, Chlorella vulgaris fo. tenia, Chlorella vulgaris* var. *autotrophica, Chlorella vulgaris* var. *viridis, Chlorella vulgaris* var. *vulgaris, Chlorella vulgaris* var. *vulgaris fo. tenia, Chlorella vulgaris* var. *vulgaris fo. viridis, Chlorella xanthella, Chlorella zofingiensis, Chlorella trebouxioides, Chlorella vulgaris, Chlorococcum infusionum, Chlorococcum* sp., *Chlorogonium, Chroomonas* sp., *Chrysosphaera* sp., *Cricosphaera* sp., *Crypthecodinium cohnii, Cryptomonas* sp., *Cyclotella cryptica, Cyclotella meneghiniana, Cyclotella* sp., *Chlamydomonas moewusii, Chlamydomonas reinhardtii, Chlamydomonas* sp., *Dunaliella* sp., *Dunaliella bardawil, Dunaliella bioculata, Dunaliella granulate, Dunaliella maritime, Dunaliella minuta, Dunaliella parva, Dunaliella peircei, Dunaliella primolecta, Dunaliella salina, Dunaliella terricola, Dunaliella tertiolecta, Dunaliella viridis, Dunaliella tertiolecta, Eremosphaera viridis, Eremosphaera* sp., *Ellipsoidon* sp., *Euglena* spp., *Franceia* sp., *Fragilaria crotonensis, Fragilaria* sp., *Gleocapsa* sp., *Gloeothamnion* sp., *Haematococcus pluvialis, Hymenomonas* sp., *Isochrysis aff. galbana, Isochrysis galbana, Lepocinclis, Micractinium, Micractinium, Monoraphidium minutum, Monoraphidium* sp., *Nannochloris* sp., *Navicula acceptata, Navicula biskanterae, Navicula pseudotenelloides, Navicula pelliculosa, Navicula saprophila, Navicula* sp., *Nephrochloris* sp., *Nephroselmis* sp., *Nitzschia communis, Nitzschia alexandrina, Nitzschia closterium, Nitzschia communis, Nitzschia dissipata, Nitzschia frustulum, Nitzschia hantzschiana, Nitzschia inconspicua, Nitzschia intermedia, Nitzschia microcephala, Nitzschia pusilla, Nitzschia pusilla elliptica, Nitzschia pusilla monoensis, Nitzschia quadrangular, Nitzschia* sp., *Ochromonas* sp., *Oocystis parva, Oocystis pusilla, Oocystis* sp., *Oscillatoria limnetica, Oscillatoria* sp., *Oscillatoria subbrevis, Parachlorella kessleri, Pascheria acidophila, Pavlova* sp., *Phaeodactylum tricornutum, Phagus, Phormidium, Platymonas* sp., *Pleurochrysis carterae, Pleurochrysis dentate, Pleurochrysis* sp., *Prototheca wickerhamii, Prototheca stagnora, Prototheca portoricensis, Prototheca moriformis, Prototheca zopfii, Pseudochlorella aquatica, Pyramimonas* sp., *Pyrobotrys, Rhodococcus opacus, Sarcinoid chrysophyte, Scenedesmus armatus, Schizochytrium, Spirogyra, Spirulina platensis, Stichococcus* sp., *Synechococcus* sp., *Synechocystis, Tagetes erecta, Tagetes patula, Tetraedron, Tetraselmis* sp., *Tetraselmis striata, Tetraselmis suecica, Thalassiosira weissflogii,* and *Viridiella fridericiana.*

Biocompatible: The term biocompatible, as used herein, refers to synthetic and/or natural material that does not have a substantial negative impact on organisms, tissues, cells, biological systems or pathways and/or protein function.

Biomass: Biomass, as used herein, refers to any algal-based organic matter that may be used for carbon storage and/or as a source of energy (e.g., biofuels).

Conduit: Conduit, as used herein, refers to a tube (e.g., flow tube), pipe, or channel having any shape that provides a structure for holding and/or guiding the flow of a liquid, solution or slurry, including but not limited to an aqueous solution containing algae or other living cells.

Expose (to): To be subject to or contacted with (directly or indirectly) a substance or physical effect (such as a magnetic field gradient).

Halbach Array: Halbach array, as used herein, refers to an arrangement of a plurality of permanent magnets placed in a specific orientation (e.g., spatially rotating pattern) that augments the magnetic field on one side of the array while canceling the field to zero on the other side of the array.

Halbach Cylinder (or ring): Halbach cylinder (or ring), as used herein, refers to a magnetized cylinder (or ring) composed of magnetic material that produces a magnetic field confined entirely within the cylinder (or ring) with zero field outside the cylinder (or ring). The cylinders (or ring) may also be magnetized such that the magnetic field is entirely outside the cylinder (or ring), with zero field inside Magnet: A magnet, as used herein, refers to any material or object that produces a magnetic field. Non-limiting examples of magnets are electromagnets and permanent magnets.

Percent Identity: Percent identity, as used herein in the context of two or more nucleic acids or peptide sequences, refer to two or more sequences or subsequences that are the same or have a specified percentage of amino acid residues or nucleotides that are the same (i.e., about 60% identity, preferably 65%, 70%, 75%, 80%, 85%, 90%, 91%, 92%, 93%, 94%, 95%, 96%, 97%, 98%, 99%, or higher identity over a specified region, when compared and aligned for maximum correspondence over a comparison window or designated region) as measured using a BLAST or BLAST 2.0 sequence comparison algorithms with default parameters described below, or by manual alignment and visual inspection.

Permanent Magnet: A permanent magnet, as used herein, refers to an object made from a material that is magnetized and creates its own persistent magnetic field absent an inducing field or electrical current.

Separate: To isolate from a mixture or to divide into constituent parts. In some examples, separating components of a mixture (such as an aqueous solution and algae) does not require absolute separation; rather it is a relative term. Thus for example, separated algae cells (for example from an aqueous solution) are ones in which the algae cells are more enriched than in the starting mixture. In some examples, algae cells are separated from an aqueous solution such that the algae cells represent at least about 20% (such as at least about 30%, 40%, 50%, 60%, 70%, 80%, 90%, 95%, 99%, or even 100%) of the total preparation after separation.

Transgenic Algae: Transgenic algae, as used herein, refer to algae whose genetic material has been altered using genetic engineering techniques so that it is no longer a "wild-type" organism. An example of genetically modified algae is transgenic algae that possess one or more genes that have been transferred to the algae from a different species (for example, a different species of algae or from bacteria or another organism). Another example is an alga wherein endogenous genes have been rearranged such that they are in a different and advantageous arrangement or amplified so that specific sequences are increased. In this example, no foreign DNA remains in the modified cell.

Tesla: The term Tesla (T), as used herein, refers to the SI derived unit of magnetic field B, also known as "magnetic flux density." One Tesla is equal to one weber per square meter.

Wild-type: In some examples as used herein, wild-type refers to the phenotype and/or genotype of the typical form of a species as it occurs in nature. In other examples, wild-type refers to the phenotype and/or genotype of a reference or laboratory strain of a species (such as algae). In some examples, a wild-type algae is a non-transgenic or non-recombinant species or strain of algae.

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. "Comprising A or B" means including A, or B, or A and B. It is further to be understood that all base sizes or amino acid sizes, and all molecular weight or molecular mass values, given for nucleic acids or polypeptides are approximate, and are provided for description.

Further, ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 (as well as fractions thereof unless the context clearly dictates otherwise). Any concentration range, percentage range, ratio range, or integer range is to be understood to include the value of any integer within the recited range and, when appropriate, fractions thereof (such as one tenth and one hundredth of an integer), unless otherwise indicated. Also, any number range recited herein relating to any physical feature, such as polymer subunits, size or thickness, are to be understood to include any integer within the recited range, unless otherwise indicated. As used herein, "about" or "consisting essentially of" mean±20% of the indicated range, value, or structure, unless otherwise indicated. As used herein, the terms "include" and "comprise" are open ended and are used synonymously.

Although methods and materials similar or equivalent to those described herein can be used in the practice or testing of the present disclosure, suitable methods and materials are described below. All publications, patent applications, patents, and other references mentioned herein are incorporated by reference in their entirety. In case of conflict, the present specification, including explanations of terms, will control. In addition, the materials, methods, and examples are illustrative only and not intended to be limiting.

III. Overview of Several Embodiments

A. Methods of Separating Algae from an Aqueous Solution

Disclosed herein are methods for separating algae from an aqueous solution which include exposing an aqueous solution containing algae and an iron supplement (such as an iron salt) to a magnetic field gradient sufficient to separate the algae from the aqueous solution. Without being bound by theory, it is believed that the method involves flocculating the algae with the iron supplement. The resulting floc is magnetic (for example, paramagnetic), allowing for the algae to be separated from the aqueous solution upon exposure to a magnetic field gradient. In some examples, the concentration or aggregation of the algae occurs very rapidly upon addition and/or mixing of an iron supplement with an aqueous solution including algae. Thus, in some embodiments, the disclosed methods do not include or require that the algae take up iron from the environment.

Iron homeostasis is a significant constraint on the welfare of all forms of life. Iron is absolutely required in several protein complexes and is toxic when exposed to oxygen in the presence of a reduced metabolic state where many forms of reactive oxygen species can be produced. As a result, a mechanism for storing iron and controlling its availability is highly desirable. Surprisingly few mechanisms have been identified. Instead a nearly ubiquitous mechanism of storing iron in ferritin or bacterioferritin complexes is present. A variety of iron transporters and reductases act to contribute to the iron pool, but ferritin and bacterioferritin are largely responsible for regulating the (bio)availability of that iron pool.

One way to take advantage of the iron homeostasis mechanism for improved algal biofuels production is to grow the algae in the presence of excess iron. Iron concentrations at or in excess of 200 micromolar (µM) are inhibitory to photoautrophic growth of $C.$ $reinhardtii$ under full sunlight. However, it is not inhibitory to growth under low light or to heterotrophic growth. Growth conditions where iron is spiked into the medium in the evening when the light levels are low permit optimal growth. The natural process of capturing iron and storing it enables photoautrophic growth when iron levels return to low levels. This condition enhances iron storage in the form of ferritin complexes. This increase in ferritin enhances magnetic susceptibility of the cell which enables magnetic manipulation.

Thus, in some embodiments, disclosed herein are methods for separating algae from an aqueous solution which utilize iron sequestered in the algae for magnetic separation of the algae from the aqueous solution. The algae take up iron from the environment (for example, an iron supplement in the aqueous solution) and in at least some examples, form magnetic nanoparticles inside the algae cells. The algae thus become sensitive to a magnetic field and can be separated from the aqueous solution using a magnet.

The disclosed methods include exposing an aqueous solution containing algae and an iron supplement (such as an iron salt) to a magnetic field gradient having sufficient strength to separate the algae from the aqueous solution. In particular examples, the iron supplement does not include iron oxide (or magnetite). In other, the iron supplement does not include magnetic particles, such as magnetic nanoparticles.

The iron salt is biocompatible with the algae. In particular examples the iron supplement in the aqueous solution is an iron salt, such as $FeSO_4$; $FeBr_2$; $FeBr_3$; $FeCl_2$; $FeCl_3$; $FeF_2$; $FeF_3$; $FeI_2$; $FeMoO_4$; $(NH_4)_2Fe(SO_4)_2.6H_2O$; $C_{20}H_{20}Cl_2FeN_4$; $FeCl_2.4H_2O$; $C_6H_5FeO_7$; $FeF_3.3H_2O$; $Fe(NO_3)_3.9H_2O$; $Fe(C_2O_4).2H_2O$; $Fe_2(C_2O_4)_3.6H_2O$; $Fe(ClO_4)_2.xH_2O$; $Fe(ClO_4)_3.H_2O$; $FePO_4.4H_2O$; $Fe_4(P_2O_7)_3$; $FeSO_4.xH_2O$; $Fe_2(SO_4)_3.xH_2O$; $Fe(BF_4)_2.6H_2O$; $K_4Fe(CN)_6.3H_2O$, or a combination of two or more thereof. In some examples, the iron salt is a ferrous salt. In one non-limiting example, the iron salt is ferrous sulfate. In other examples, the iron salt is a ferric salt. One of skill in the art can select additional iron salts useful for the methods disclosed herein.

The iron salt is included in the aqueous solution with the algae at a concentration sufficient for the algae to take up iron from the solution and to be separated from the aqueous solution when exposed to a magnetic field. In particular examples, the iron salt is included in the aqueous solution at a concentration of about 100 µM to 2 mM (such as about 100 µM to 500 µM, about 200 µM to 1.5 mM, about 300 µM to 1 mM, or about 500 µM to 1 mM). For example, the iron salt may be included in the aqueous solution at a concentration of about 100 µM, about 300 µM, about 500 µM, or about 1 mM.

In some examples, the aqueous solution containing the algae is contacted with an iron supplement essentially immediately prior to exposing the aqueous solution containing the algae and iron supplement to the magnetic field gradient. For example, the aqueous solution containing the algae is mixed with an iron supplement and is exposed to a magnetic field gradient as soon as mixing is complete (for example, within about 10 minutes or less of addition of the iron supplement). In other examples, the aqueous solution containing the algae includes the iron supplement for at least about 15 minutes or more prior to exposing the solution, algae, and iron supplement mixture to the magnetic field gradient, such as for at least 30 minutes, at least about 1 hour, at least about 90 minutes, at least about 2 hours, at least about 3 hours, at least about 6 hours, at least about 12 hours, at least about 16 hours, at least about 24 hours, or more. In some examples, the aqueous solution containing the algae includes the iron supplement for about 15 minutes to about 72 hours (such as about 30 minutes to 48 hours, about 1 hour to 24 hours, about 3 hours to 72 hours, or about 6 hours to 24 hours).

The algae are separated from the aqueous solution by exposing the aqueous solution containing the algae and the iron supplement to a magnetic field gradient. The magnetic field gradient is of sufficient strength to separate the algae from the aqueous solution, for example, such that the algae cells represent at least about 20% (such as at least 30%, 40%, 50%, 60%, 70%, 80%, 90%, 95%, 99%, or even 100%) of the total preparation after separation. In some examples, the magnetic field gradient is about 50 Tesla/meter to about 2000 Tesla/meter (such as about 100 Tesla/meter to about 500 Tesla/meter, about 200 Tesla/meter to about 600 Tesla/meter, about 500 Tesla/meter to about 1500 Tesla/meter, about 300 Tesla/meter to about 1000 Tesla/meter, or about 500 Tesla/meter to about 1000 Tesla/meter). In particular examples, the magnetic field gradient is at least about 50 Tesla/meter, about 100 Tesla/meter, about 200 Tesla/meter, about 300 Tesla/meter, about 400 Tesla/meter, about 500 Tesla/meter, about 600 Tesla/meter, about 700 Tesla/meter, about 800 Tesla/meter, about 900 Tesla/meter, or about 1000 Tesla/meter. The magnetic field gradient can be generated using any means, including but not limited to permanent magnet(s), electromagnet(s), Halbach array(s) or cylinder(s), or any combination thereof. In other examples, the magnetic field gradient is generated with a permanent magnet circuit. For example, one or more permanent magnets and optionally one or more pole pieces are arranged to provide a field gradient suitable for separation of algae from the solution using the methods described herein.

The aqueous solution including the algae and the iron supplement is placed at a distance from the magnet such that the magnetic field gradient causes separation of the algae (for example, algae containing iron) from the aqueous solution. In some examples, the solution is placed about 5 cm or less from the magnet (for example, about 4 cm or less, about 3 cm or less, about 2 cm or less, about 1 cm or less, or about 0.5 cm or less from the magnet). One of skill in the art can select an appropriate distance between the aqueous solution and the magnet, for example, based at least in part on the strength of the magnetic field gradient, the type of algae, and/or the amount or type of iron supplement present in the aqueous solution. In some examples, the methods include flowing an aqueous solution containing algae cells and an iron supplement through a magnetic field gradient. For example, the aqueous solution containing the algae flow or passes through a container (such as a tube, conduit, flask, or other vessel) within close proximity to a magnet (for example, at a distance such that the magnetic field gradient separates the algae from the aqueous solution). In some examples, the aqueous solution containing the algae is passed through a tube or conduit about less than about 1 cm in diameter (for example, less than 9 mm, less than 8 mm, less than 7 mm, less than 6 mm, less than 5 mm, less than 4 mm, less than 3 mm, less than 2 mm, or less than 1 mm). In other examples, the tube or conduit is more than about 1 cm (for example, about 1 cm to 500 cm, about 1 cm to about 10 cm, about 2 cm to about 20 cm, about 10 cm to 250 cm, or about 50 cm to 100 cm). The flow rate is selected such that the algae are exposed to the magnetic field gradient for a sufficient time to separate the algae from the aqueous solution. In some examples, the flow rate is about 10 µl/minute to about 100 ml/minute (such as about 100 µl/minute to 10 ml/minute, about 250 µl/minute to 5 ml/minute, about 1 ml/minute to 5 ml/minute, or about 100 µl/minute to 500 µl/minute). In one non-limiting example, the aqueous solution containing the algae is passed through a transfer tube having a diameter of about 1 mm at a flow rate of about 250 µl/minute where the transfer tube is less than 1 cm from the magnet. In other examples, the methods include exposing a vessel (such as a tube, flask, photobioreactor, or other container) containing the aqueous solution and algae to a magnetic field gradient and separating the algae from the aqueous solution. In some examples, the magnetic field gradient is at the bottom of the vessel and the algae are collected at the bottom of the vessel. However, any form of magnetic collection or separation now known or developed in the future may be used.

In particular examples, the methods disclosed herein further include culturing algae in an aqueous solution containing an iron supplement (such as one or more of the iron salts described above) for a period of time prior to exposing the aqueous solution containing the algae and iron supplement to a magnetic field gradient. The algae are cultured in the presence of the iron supplement for a sufficient period of time for the algae to flocculate or aggregate, or to take up or accumulate iron intracellularly. The algae cells may also divide during this period of time, increasing the number of algae cells in the aqueous solution. In some examples, the algae are cultured in the aqueous solution with the iron supplement for about 1 hour to 7 days (such as about 1 hour to 72 hours, about 6 hours to 48 hours, about 12 hours to 36 hours, about 1 day to 7 days, or about 2 days to 5 days). In some examples, the algae are cultured in the presence of the iron supplement for at least about 1 hour, 6 hours, 12 hours, 24 hours, 36 hours, or more.

The separated algae (for example, algae that are collected at or near the magnetic field gradient) can be collected by any convenient method. In some examples, the separated algae are collected by removing the magnetic field gradient and flushing out the separated algae. In other examples, the separated algae are collected using magnetic diversion, for example by using a system with a magnetic field gradient and two outlets, where the algae are collected through one outlet due to the magnetic field gradient near the outlet and the aqueous solution is collected through a second outlet where the magnetic field gradient is weaker or absent.

The separated algae can be used for lipid extraction (for example, for biofuel production) or extraction of other products of interest (including food products or supplements). In some examples, the separated algae are lysed and optionally products of interest are isolated. Methods of lysing algae cells include sonication or mechanical disruption (for example, using a French press or glass beads). In other examples, separation of algae from an aqueous solution can be used to purify water or for bioremediation (for example, algae take up undesirable compounds from a solution, which can then be removed by separating the algae from the solution).

B. Algae

Disclosed herein are methods and systems for separating algae cells from an aqueous solution containing the algae. Algae that can be used in the disclosed methods and systems include, but are not limited to *Achnanthes orientalis*, *Agmenellum* spp., *Amphiprora hyaline*, *Amphora coffeiformis*, *Amphora coffeiformis* var. *linea*, *Amphora coffeiformis* var. *punctata*, *Amphora coffeiformis* var. *taylori*, *Amphora coffeiformis* var. *tenuis*, *Amphora delicatissima*. *Amphora delicatissima* var. *capitata*, *Amphora* sp., *Anabaena*, *Ankistrodesmus*, *Ankistrodesmus falcatus*, *Boekelovia hooglandii*, *Borodinella* sp., *Botryococcus braunii*, *Botryococcus sudeticus*, *Bracteococcus minor*, *Bracteococcus medionucleatus*, *Carteria*, *Chaetoceros gracilis*, *Chaetoceros muelleri*, *Chaetoceros muelleri* var. *subsalsum*, *Chaetoceros* sp., *Chlamydomonas perigranulata*, *Chlorella anitrata*, *Chlorella antarctica*, *Chlorella aureoviridis*, *Chlorella Candida*, *Chlorella capsulate*, *Chlorella desiccate*, *Chlorella ellipsoidea*, *Chlorella emersonii*, *Chlorella fusca*, *Chlorella fusca* var. *vacuolata*, *Chlorella glucotropha*, *Chlorella infusionum*, *Chlorella infusionum* var. *actophila*, *Chlorella infusionum* var. *auxenophila*, *Chlorella kessleri*, *Chlorella lobophora*, *Chlorella luteoviridis*, *Chlorella luteoviridis* var. *aureoviridis*, *Chlorella luteoviridis* var. *lutescens*, *Chlorella miniata*, *Chlorella minutissima*, *Chlorella mutabilis*, *Chlorella nocturna*, *Chlorella ovalis*, *Chlorella parva*, *Chlorella photophila*, *Chlorella pringsheimii*, *Chlorella protothecoides*, *Chlorella protothecoides* var. *acidicola*, *Chlorella regularis*, *Chlorella regularis* var. *minima*, *Chlorella regularis* var. *umbricata*, *Chlorella reisiglii*, *Chlorella saccharophila*, *Chlorella saccharophila* var. *ellipsoidea*, *Chlorella salina*, *Chlorella simplex*, *Chlorella sorokiniana*, *Chlorella* sp., *Chlorella sphaerica*, *Chlorella stigmatophora*, *Chlorella vanniellii*, *Chlorella vulgaris*, *Chlorella vulgaris fo. tenia*, *Chlorella vulgaris* var. *autotrophica*, *Chlorella vulgaris* var. *viridis*, *Chlorella vulgaris* var. *vulgaris*, *Chlorella vulgaris* var. *vulgaris fo. tenia*, *Chlorella vulgaris* var. *vulgaris fo. viridis*, *Chlorella xanthella*, *Chlorella zofingiensis*, *Chlorella trebouxioides*, *Chlorella vulgaris*, *Chlorococcum infusionum*, *Chlorococcum* sp., *Chlorogonium*, *Chroomonas* sp., *Chrysosphaera* sp., *Cricosphaera* sp., *Crypthecodinium cohnii*, *Cryptomonas* sp., *Cyclotella cryptica*, *Cyclotella meneghiniana*, *Cyclotella* sp., *Chlamydomonas moewusii* *Chlamydomonas reinhardtii*, *Chlamydomonas* sp., *Dunaliella* sp., *Dunaliella bardawil*, *Dunaliella bioculata*, *Dunaliella granulate*, *Dunaliella maritime*, *Dunaliella minuta*, *Dunaliella parva*, *Dunaliella peircei*, *Dunaliella primolecta*, *Dunaliella salina*, *Dunaliella terricola*, *Dunaliella tertiolecta*, *Dunaliella viridis*, *Dunaliella tertiolecta*, *Eremosphaera viridis*, *Eremosphaera* sp., *Ellipsoidon* sp., *Euglena* spp., *Franceia* sp., *Fragilaria crotonensis*, *Fragilaria* sp., *Gleocapsa* sp., *Gloeothamnion* sp., *Haematococcus pluvialis*, *Hymenomonas* sp., *Isochrysis aff. galbana*, *Isochrysis galbana*, *Lepocinclis*, *Micractinium*, *Micractinium*, *Monoraphidium minutum*, *Monoraphidium* sp., *Nannochloris* sp., *Navicula acceptata*, *Navicula biskanterae*, *Navicula pseudotenelloides*, *Navicula pelliculosa*, *Navicula saprophila*, *Navicula* sp., *Nephrochloris* sp., *Nephroselmis* sp., *Nitzschia communis*, *Nitzschia alexandrina*, *Nitzschia closterium*, *Nitzschia communis*, *Nitzschia dissipata*, *Nitzschia frustulum*, *Nitzschia hantzschiana*, *Nitzschia inconspicua*, *Nitzschia intermedia*, *Nitzschia microcephala*, *Nitzschia pusilla*, *Nitzschia pusilla elliptica*, *Nitzschia pusilla monoensis*, *Nitzschia quadrangular*, *Nitzschia* sp., *Ochromonas* sp., *Oocystis parva*, *Oocystis pusilla*, *Oocystis* sp., *Oscillatoria limnetica*, *Oscillatoria* sp., *Oscillatoria subbrevis*, *Parachlorella kessleri*, *Pascheria acidophila*, *Pavlova* sp., *Phaeodactylum tricornutum*, *Phagus*, *Phormidium*, *Platymonas* sp., *Pleurochrysis carterae*, *Pleurochrysis dentate*, *Pleurochrysis* sp., *Prototheca wickerhamii*, *Prototheca stagnora*, *Prototheca portoricensis*, *Prototheca moriformis*, *Prototheca zopfii*, *Pseudochlorella aquatica*, *Pyramimonas* sp., *Pyrobotrys*, *Rhodococcus opacus*, *Sarcinoid chrysophyte*, *Scenedesmus armatus*, *Schizochytrium*, *Spirogyra*, *Spirulina platensis*, *Stichococcus* sp., *Synechococcus* sp., *Synechocystis*, *Tagetes erecta*, *Tagetes patula*, *Tetraedron*, *Tetraselmis* sp., *Tetraselmis striata*, *Tetraselmis suecica*, *Thalassiosira weissflogii*, and *Viridiella fridericiana*. In a particular non-limiting example, the algae is *Tetraselmis striata*.

In some embodiments, the algae are wild-type algae cells. Wild-type algae cells have the phenotype and/or genotype of the typical form of a species as it occurs in nature or in a cultured/laboratory setting, and are not genetically modified (for example, are not recombinant or transgenic algae cells). Wild-type algae include algae isolated from the environment (for example, ponds, lakes, streams, rivers, seas, oceans, and so on). In additional examples, wild-type algae also include reference or laboratory strains, which may have standard or accepted characteristics, but which differ from algae isolated from the environment. Thus, in some examples, wild-type algae include algae available from collections, such as UTEX: The Culture Collection of Algae (Austin, Tex.) or the American Type Culture Collection (Manassas, Va.). In other examples, wild-type algae are non-transgenic or non-recombinant (for example, non-genetically modified) algae.

In other examples, the algae are transgenic algae (such as recombinant or genetically modified algae). In some examples, the algae are recombinant algae expressing one or more genes that increase iron uptake by the algae. See, e.g., U.S. Pat. App. Publ. No. 2013/0210064. In further examples, the algae are transgenic algae expressing one or more genes that permit or increase production of compounds of interest. See, e.g., U.S. Pat. App. Publ. No. 2012/0196339.

Methods for the transformation of various types of algae are known to those skilled in the art. See for example Radakovits et al., *Eukaryotic Cell*, 9, 486-501 (2010), which is incorporated herein by reference. The transformation of the chloroplast genome was the earliest method and is well documented in the literature (Kindle et al., *Proc Natl Acad Sci.*, 88, p. 1721-1725 (1991)). A variety of methods have been used to transfer DNA into microalgal cells, including but not limited to agitation in the presence of glass beads or silicon carbide whiskers, electroporation, biolistic microparticle bombardment, and *Agrobacterium tumefaciens*-mediated gene transfer. A preferred method of transformation for the present invention is biolistic microparticle bombardment, carried out with a device referred to as a "gene gun."

Different regions of the alga may be targeted for transformation in different embodiments of the invention. Target regions include the nuclear genome, the mitochondrial genome, and the chloroplast genome. The preferred target region can vary depending on the gene being expressed. For example, if an alga has been modified to express a lethal gene that is obtained from a bacterium, it may be preferable to express the lethal gene in the chloroplast or mitochondrion, as these organelles evolved from bacteria and retain many similarities. This can be achieved using a chloroplast expression vector that employs two intergenic regions of the chloroplast genome that flank and drive the site-specific integration of a transgene cassette (5' untranslated region, or 5' UTR followed by the coding sequence of the protein to be expressed which can drive the biological function desired, followed by a 3' UTR. The 5 'UTR contains a cis acting site that allows docking of the RNA polymerase that drives transcription of the transgene. The 3' UTR contains sequence that allows for the correct termination of the transcription by RNA polymerase. However, in other cases, such as when the essential or lethal gene has an effect in various regions of the cell, it may be preferable to express the gene in the nucleus if the algae are eukaryotic. This can be achieved with a gene cassette that employs a eukaryotic promoter sequence upstream of the protein coding sequence and a eukaryotic termination sequence downstream of the protein coding sequence.

Genetically modified algae can be transformed to include an expression cassette. An expression cassette is made up of one or more genes and the sequences controlling their expression. The three main components of a nuclear expression cassette are a promoter sequence, an open reading frame expressing the gene, and a 3' untranslated region, which may contain a polyadenylation. The cassette is part of vector DNA used for transformation. The promoter is operably linked to the gene expressed represented by the open reading frame.

C. Systems for Separating Algae from an Aqueous Solution

Also disclosed herein are systems for separating algae from an aqueous solution. In some embodiments, the system includes a source comprising an aqueous solution containing algae and at least one conduit that carries the aqueous solution containing the algae from the source, wherein the at least one conduit is in close proximity to a magnet having a magnetic field gradient having sufficient strength to separate the algae from the aqueous solution and wherein the algae are collected in the conduit. In some examples, the system includes two or more conduits, each connected to the source, which carry the aqueous solution and algae in close proximity to a magnet having a magnetic field gradient having sufficient strength to separate the algae from the aqueous solution. For example, the system may include two or more (such as 3, 4, 5, 10, 20, or more) conduits that run in parallel from the source in close proximity to the magnet. In some examples, the source is a vessel or container (such as a tube, flask, or bioreactor) containing the aqueous solution and algae. In other examples, the source is a pond, raceway, or other body of water containing algae. The source, the at least one conduit, or both contain an iron salt (such as those discussed above). The iron salt, its concentration, and the magnetic field gradient can be selected by one of ordinary skill in the art, including those described in Section A, above. Thus, in some examples, the system also includes one or more magnets (such as one or more permanent magnets, permanent magnet circuits, electromagnets, or Halbach array or cylinders). The aqueous solution continuing the algae (and optionally the iron salt) is moved from the source to the at least one conduit with a pump, by gravity, or using any suitable means for moving fluids or cell suspension.

In other embodiments, the system includes a source continuing an aqueous solution and an iron supplement, a first conduit having a first volume-carrying capacity connected to the source and a second conduit having a second volume-carrying capacity connected to the first conduit. The first conduit carries the aqueous solution continuing the algae and the iron supplement from the source to the second conduit. The second conduit passes near a magnet having a magnetic field gradient having sufficient strength to separate the algae from the aqueous solution and the algae are collected in the second conduit by exposure to the magnetic field gradient. In some examples, the method includes at least one additional conduit in parallel with the second conduit, which carry the aqueous solution and algae from the first conduit and pass near the magnet. In some examples, the source is a vessel or container (such as a tube, flask, or bioreactor) containing the aqueous solution and algae. In other examples, the source is a pond, raceway, or other body of water containing algae. The source, the first conduit, the second conduit, or any combination thereof contains an iron salt (such as those discussed above). The iron salt, its concentration, and the magnetic field gradient can be selected by one of ordinary skill in the art, including those described in Section A, above. Thus, in some examples, the system also includes one or more magnets (such as one or more permanent magnets, electromagnets, or Halbach array or cylinders). In some examples, the volume-carrying capacity of the second conduit is greater than the volume-carrying capacity of the first conduit. In other examples, the volume-carrying capacity of both the first and second conduits is approximately the same.

The following examples are provided to illustrate certain particular features and/or embodiments. These examples should not be construed to limit the disclosure to the particular features or embodiments described.

EXAMPLES

Example 1

Growth and Harvesting of Algae Via Magnetic Separation

This example provides methods and conditions for culturing algae with ferrous ion based salts and harvesting the algae using a permanent magnet. Briefly, the addition of the ferrous ion based salt to the algae culture results in flocculation of the algae, and the matrix that is responsible for the flocculation is magnetic. Thus, by applying a magnetic field to the flocculated algae, the algae are collected from a solution using a magnet.

*Tetraselmis striata* was isolated from a mixed pond sample and grown as an axenic culture. Species identification was performed by PCR and sequencing of the 18S RNA and compared to the known algae sequence 18S database in NCBI.

Algae were grown in F/2 media (National Center for Marine Algae and Microbiota, East Boothbay, Me.) with appropriate lighting and $CO_2$ supply. $FeSO_4 \cdot 7H_2O$ (Sigma-Aldrich, St. Louis, Mo.) was added to different algae cultures at concentrations ranging from 100 to 1000 µmols/Liter Immediately after the addition of the ferric salt to the cultures, small flocs were observed under a light microscope (FIG. 1).

Figure 2:
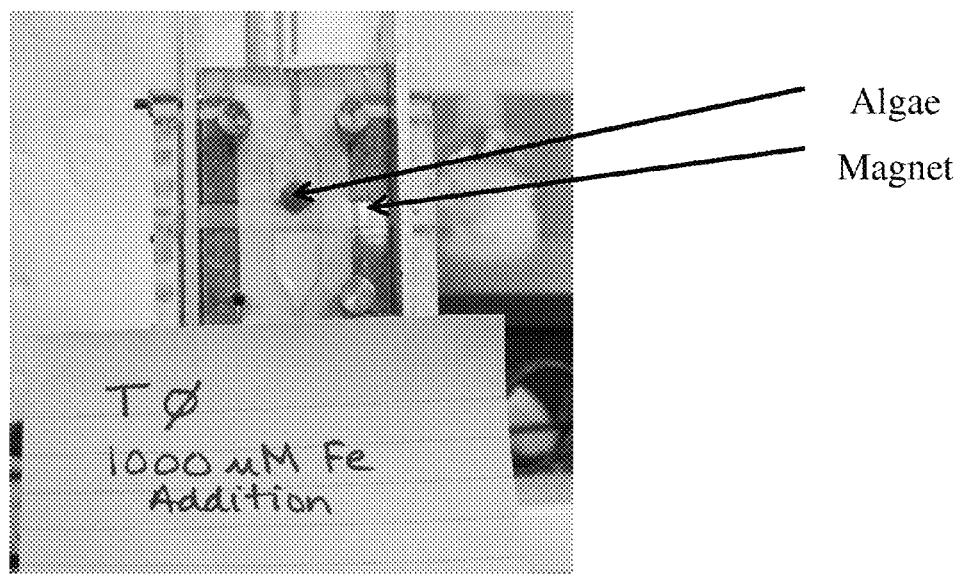
FIG. 2 shows magnetic separation of algae from the flow solution at time 0 (T0) after the addition of 1000 µM ferric salts to the algae culture. Algae accumulated at or near the horizontal magnet (~650 Tesla/m).
Figure 3:
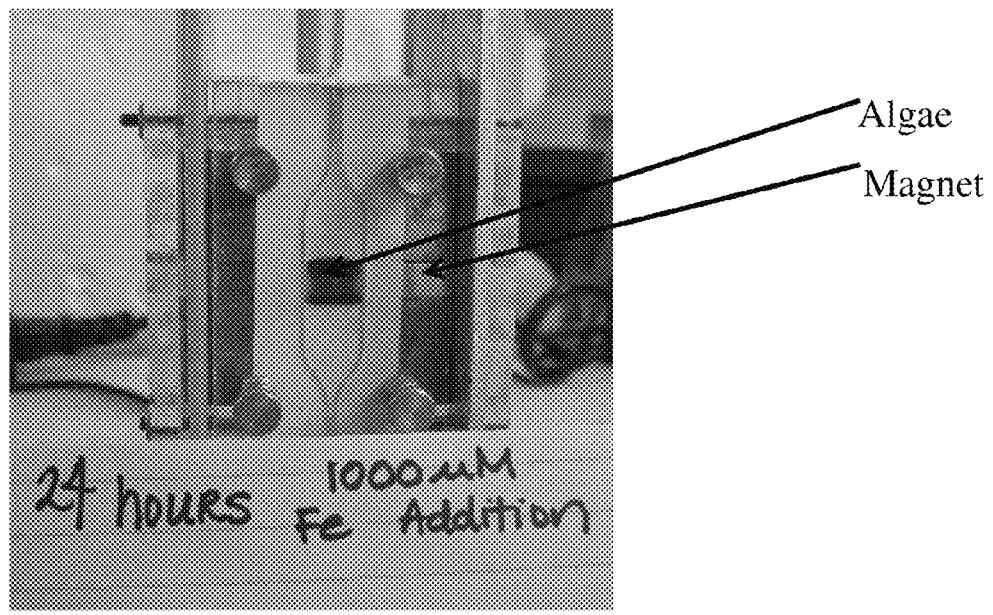
FIG. 3 shows magnetic separation of algae from the flow solution at time 24 (T24) after the addition of 1000 µM ferric salts to the algae culture. Algae accumulated at or near the horizontal magnet (~650 Tesla/m).

The algae ferric salt cultures were exposed to a permanent magnet having a magnetic field gradient of about 650 Tesla/meter by passing the liquid cultures through a transfer tube having a diameter of about 1 mm at a flow rate of about 250 µL/minute within close proximity to the magnet (the transfer tube being adjacent to the magnet or less than 1 cm from the magnet). Algae were separated from the flow solution at various ferric salt concentrations and times. Table 1 below shows the relative separation. Separation was observed at time 0 (T0) with the addition of 1000 µM ferric salts (FIG. 2), and time 24 hours (T24) with the addition of 1000 µM ferric salts (FIG. 3). Greater separation was observed at T24 compared to the separation observed at T0.

TABLE 1

| Time | 0 µM $Fe^{+2}$ Salt | 100 nM $Fe^{+2}$ Salt | 300 µM $Fe^{+2}$ Salt | 1000 µM $Fe^{+2}$ Salt |
|---|---|---|---|---|
| 0 hr. | − | − | + | +++ |
| 1 hr. | ND | + | ND | ND |
| 3 hrs. | ND | ND | + | ND |
| 24 hrs. | − | + | +++ | +++++ |

Figure 4:
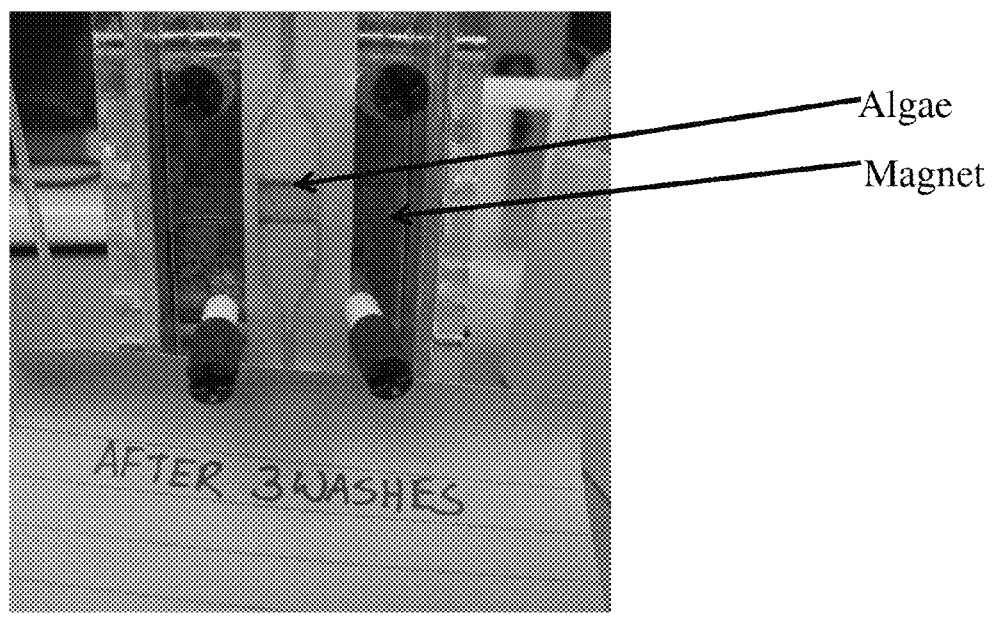
FIG. 4 shows magnetic separation of algae from the flow solution at time 24 (T24) after the addition of 1000 µM ferric salts to the algae culture, followed by sample dilution of approximately 10-fold. Algae accumulated at or near the horizontal magnet (~650 Tesla/m).

"+" = relative capture of algae at magnet; N.D. = no data; "−" = no observable capture To determine if algae exposed to ferric salts would maintain the ability to be harvested via exposure to a magnet after diluting the ferric salts in the culture solution, the algae were washed three times (~10-fold dilution of cultures compared to original ferric salt cultures). Even after diluting the cultures, algae were separated from the flow solution using a permanent magnet (FIG. 4).

These data show that algae may be harvested by magnetic separation after culturing the algae with iron salts.

In view of the many possible embodiments to which the principles of the disclosure may be applied, it should be recognized that the illustrated embodiments are only examples and should not be taken as limiting the scope of the invention. Rather, the scope of the invention is defined by the following claims. We therefore claim as our invention all that comes within the scope and spirit of these claims.

We claim:

1. A method comprising:
    adding an iron salt to an algae culture in aqueous solution, wherein the iron salt is selected from the group consisting of $FeSO_4$; $FeBr_2$; $FeBr_3$; $FeCl_2$; $FeCl_3$; $FeF_2$; $FeF_3$; $FeI_2$; $FeMoO_4$; $(NH_4)_2Fe(SO_4)_2.6H_2O$; $C_{20}H_{20}Cl_2FeN_4$; $FeCl_2.4H_2O$; $C_6H_5FeO_7$; $FeF_3.3H_2O$; $Fe(NO_3)_3.9H_2O$; $Fe(C_2O_4).2H_2O$; $Fe_2(C_2O_4)_3.6H_2O$; $FePO_4.4H_2O$; $Fe_4(P_2O_7)_3$; $FeSO_4.7H_2O$; $Fe(BF_4)_2.6H_2O$; $K_4Fe(CN)_6.3H_2O$ and a combination of two or more thereof, and the iron salt in the aqueous solution is at a concentration of from 100 μM to 1000 μM;
    culturing the algae in the aqueous solution with iron salt for at least 24 hours; and
    exposing the aqueous solution comprising the cultured algae and the iron salt to a magnetic field gradient generated by a permanent magnet having sufficient strength to separate the algae from the aqueous solution, whereby the method results in the algae being separated from the aqueous solution.

2. The method of claim 1, wherein the iron salt in the aqueous solution comprises $FeSO_4$ or $FeSO_4.7H_2O$.

3. The method of claim 1, wherein the magnetic field gradient is at least about 500 Tesla/meter.

4. The method of claim 3, wherein the magnetic field gradient is at least about 1000 Tesla/meter.

5. The method of claim 1, wherein the algae comprises a wild-type algae or a transgenic algae.

6. The method of claim 5, wherein the algae comprises *Tetraselmis striata*.

* * * * *